United States Patent
Knaust et al.

(10) Patent No.: US 10,346,921 B2
(45) Date of Patent: Jul. 9, 2019

(54) PARAMETRIC SYSTEM FOR RISK SHARING OF CRITICAL ILLNESS RISKS AND CORRESPONDING METHOD THEREOF

(71) Applicant: SWISS REINSURANCE COMPANY LTD., Zurich (CH)

(72) Inventors: Timothy John Knaust, Gillingham (GB); David Thomas Ferguson, Sevenoaks (GB); Nicola Plews, London (GB); Alan James Dott, Ipswich (GB); Helen Elizabeth Chung Patterson, Datchet (GB)

(73) Assignee: Swiss Reinsurance Company Ltd., Zurich (CH)

( * ) Notice: Subject to any disclaimer, the term of this patent is extended or adjusted under 35 U.S.C. 154(b) by 607 days.

(21) Appl. No.: 14/514,189

(22) Filed: Oct. 14, 2014

(65) Prior Publication Data

US 2015/0112735 A1   Apr. 23, 2015

Related U.S. Application Data

(63) Continuation of application No. PCT/EP2013/071864, filed on Oct. 18, 2013.

(51) Int. Cl.
*G06Q 40/08* (2012.01)
*G16H 50/30* (2018.01)
*G06F 19/00* (2018.01)

(52) U.S. Cl.
CPC ............. *G06Q 40/08* (2013.01); *G06F 19/00* (2013.01); *G16H 50/30* (2018.01)

(58) Field of Classification Search
CPC ..................................................... G06Q 40/00

(Continued)

(56) References Cited

U.S. PATENT DOCUMENTS 8,452,620 B1   5/2013  Grundfest
2005/0075910 A1*  4/2005  Solankl .................. G06Q 40/08
                                                      705/4

(Continued)

OTHER PUBLICATIONS

U.S. Appl. No. 14/514,154, filed Oct. 14, 2014, Kanust, et al.

(Continued)

*Primary Examiner* — Scott S Trotter
(74) *Attorney, Agent, or Firm* — Oblon, McClelland, Maier & Neustadt, L.L.P.

(57) ABSTRACT

Proposed are a parametric, event-driven critical illness insurance system based on a resource-pooling system (1) and method for risk sharing of critical illness risks of a variable number of risk exposure components (21, 22, 23) by providing a dynamic self-sufficient risk protection for the risk exposure components (21, 22, 23) by means of the resource-pooling system (1). The resource-pooling system (1) comprises an assembly module (5) to process risk-related component data (211,221,231) and to provide the likelihood (212, 222, 232) of said risk exposure for one or a plurality of the pooled risk exposure components (21, 22, 23, . . . ) based on the risk-related component data (211, 221, 231). The risk exposure components (21,22,23) are connected to the resource-pooling system (1) for the pooling of their risks and resources, and wherein the resource-pooling system (1) comprises an multiple event-driven core-engine (3) with critical illness triggers (31, 32, 33) triggering in a patient dataflow pathway (213,223,233) to provide risk protection for a specific risk exposure component (21,22,23). The operation of the resource pooling system (1) is further supported by a parametric risk-cover related to multiple occurrences of critical illness parameters 71,72,73 triggered in the related patient data flow pathway (213, 223, 233).

34 Claims, 4 Drawing Sheets

(58) Field of Classification Search
USPC .......................................................... 705/4
See application file for complete search history.

(56) References Cited

OTHER PUBLICATIONS

U.S. Appl. No. 14/325,022, filed Jul. 7, 2014, Knaust, et al.
International Preliminary Report on Patentability with Annexes dated Feb. 16, 2016 in PCT/EP2013/071864 filed Oct. 18, 2013.

* cited by examiner

PARAMETRIC SYSTEM FOR RISK SHARING OF CRITICAL ILLNESS RISKS AND CORRESPONDING METHOD THEREOF

CROSS REFERENCE TO RELATED APPLICATION

This application is a Continuation of PCT International Application No. PCT/EP2013/071864, filed on Oct. 18, 2013, the entire contents of which are incorporated herein by reference.

FIELD OF THE INVENTION

The present invention relates to resource-pooling systems for providing risk sharing of critical illness risks of a variable number of risk exposure components by providing a dynamic self-sufficient risk protection for the risk exposure components by means of the critical illness insurance system. In particular, the invention relates to automated event-driven systems triggering on the patient dataflow pathway.

BACKGROUND OF THE INVENTION

These days, there is significant risk exposure related to many aspects in life and non-life sectors. Risk exposed units as any kinds of objects, individuals, corporate bodies and/or legal entities, necessarily are confronted with many forms of active and passive risk management to hedge and protect against the risk of certain losses and events. In the prior art, one way to address such risk of loss is based on transferring and pooling the risk of loss from a plurality of risk exposed entities to a dedicated pooling entity. In essence, this can be executed by effectively allocating the risk of loss to this pooling unit or entity by pooling resources of associated units, which are exposed to a certain risk. In case, that one of the units is hit by an event occurring related to a transferred risk, the pooling entity directly intercepts the loss or damage caused by the event by transferring resources from the pooled resources to the affected unit. Pooling of resources can be achieved by exchanging predefined amounts of resources with the resource-pooling system; e.g. payments or premiums to be paid, for the transfer of the risk. This means that predefined amounts of resources are exchanged for the other unit assuming the risk of loss.

For living individuals, a special kind of risk is based on the risk of loss of life and related possible losses; i.e., losses that occur as a consequence of the death of that individual. Such risks are traditionally handled by so-called life insurance systems. To administer a loss for benefits provided by a life insurance policy, a substantial amount of information must be collected and managed by the pooling entity in order to allow risk-transfer. Appropriate documentation must be identified, captured and analyzed, such as death certificates or medical provider verification of condition or service in the cases of health/supplementary health. One important problem arises by the fact that life insurance methods are triggered by the death of the unit, which risk is transferred. However, often problems arise for an individual before then, in that financial resources were threatened by losses occurring prior to death as a consequence of the events leading to death. This is mostly the case when the individual suffers from potentially terminal disease, like malignant cancer, which may inevitably lead to the death of the individual. Typically, the patient is confronted with increasing costs for medical treatment or other related costs as travel expenses or additional heating costs, but also by the decreasing ability to earn the money needed to fulfill their monthly financial needs. This may lead to the necessity of having to make many sacrifices; e.g. taking children out of private schools, selling their house and filling for bankruptcy. All these financial concerns contrariwise impacted on their health. Recovery is delayed, stress additionally aggravates the anyway poor health.

As a solution, resource-pooling systems were developed that cover such "critical illnesses", where the resource-pooling unit operated by the insurer provides a lump sum cash payment if the risk-exposed unit, which is, seen from the perspective of the insurer the policyholder, is diagnosed with one of the critical illnesses listed in a defined table of transferred risk. The operation of the resource-pooling system may also be structured to pay out regular income, and the payouts may also benefit the policyholder undergoing a surgical procedure, for example, having a heart bypass operation. Typically, such systems require the risk-exposed unit to survive a minimum number of days (the so-called survival period) from when the illness was first diagnosed. The survival period can vary; however, 14 days is the most commonly used survival period used. In the Australian market, survival periods are set between 8-14 days. However, systems as e.g. automated systems associated with indemnity based on accelerated payment (e.g. related to specific life insurance products) and stand alone products, are also known. The terms, as defined for the risk transfer, typically contain specific predefined triggers or rules to be applied that provide the basis for the determination of when a diagnosis of a critical illness is considered valid. Terms for survival periods may also define parameters providing that the diagnosis need to be made by a physician who specializes in the treatment of that illness or condition or name specific tests, e.g. ECG changes in case of a myocardial infarctions, that confirm the diagnosis. In many markets, the trigger parameters for many of the diseases and conditions have become standardized; thus typically resource-pooling systems would use the same definition (cf. stand alone products and accelerated critical illness systems). The standardization of the critical illness definitions serves many purposes, including better clarity of coverage for the risk-exposed units and greater comparability of terms and conditions for risk transfers among different resource-pooling systems. Such terms and conditions are often defined in the policy covering the risk transfer. For example, in the UK the Association of British Insurers (ABI) has issued a Statement of Best Practice, which includes a number of standard definitions for common critical illnesses. The prior art also provides for alternative methods of critical illness risk transfer, other than the lump sum cash payment method. These critical illness insurance systems can directly pay health providers (as e.g. "tiers payant" systems) for the treatment costs involving critical and life-threatening illnesses that are covered by the policyholder's insurance policy, including fees for specialists and procedures at a select group of high-ranking hospitals up to a certain amount per course of treatment as set out in the policy, but also transfer the payment to the customer.

In the prior art, critical illnesses are typically covered by critical illness risk transfer; these are heart attack, cancer, stroke and coronary artery by-pass surgery. Examples of other conditions that might be covered include: Alzheimer's disease, blindness, deafness, kidney failure, major organ transplant, multiple sclerosis, HIV/AIDS contracted by blood transfusion or during an operation, Parkinson's disease, paralysis of limb, terminal illness. One of the problems of the risk transfer system as provided by the prior art lies in the fact that the incidence of a condition may vary (i.e. in- or decrease) over time, and that diagnosis and treatment may improve over time, that the financial need to cover some illnesses deemed critical a decade ago is no longer considered necessary today. Likewise, some of the conditions covered today may no longer need to be covered a decade or so from now. It is very difficult to adapt the prior art systems to such changing conditions. What is clear is the fact that the financial hardship at the time of diagnosis and afterwards increases during the course of treatment, which seldom can be meet by the present systems. Furthermore, operating the systems of the prior art requires a high level of human resources, because these systems cannot be adequately automated. Therefore, a large quantity of the pooled resources are used by the resource-pooling system itself to administer the risk transfer, which makes the risk transfer expensive for the risk-exposed unit. Finally, another problem comes from the fact that, due to the medical progress, many patients no longer die but can survive for many years after undergoing treatment for a heart attack, stroke and cancer. Due to the long survival period, such individuals, who were struck already once by a critical illness, continue to be exposed to the risk of a second or consequential occurrence of a critical illness. In fact, the risk typically does not decrease, since the health of these patients is already weakened by the first incidence of a critical illness. Since critical illnesses are traditionally meant to lead to death, the risk involving such individuals, who may be affected by a second or even more critical illnesses is no longer covered by the resource-pooling system. Therefore, although the patient survived his first bout with a critical illness, he may, at least financially, not survive the second time.

SUMMARY OF THE INVENTION

It is an object of the invention to provide a system and method for risk sharing of critical illness risks of a variable number of risk exposure components by providing a dynamic self-sufficient risk protection for the risk exposure components by means of a resource-pooling system. The resource-pooling system, realized as an automated critical illness insurance system shall be completely automated and self-adaptable/self-maintaining by its technical means and shall provide the technical risk transfer basis, which can be used by service providers in the risk transfer or insurance technology for risk transfer related to critical illness risks (CI). A further object of the invention provides for a way to technically capture, handle and automate complex related operations of the insurance industry related to critical illness risk transfer. Another object is to synchronize and adjust such operations based on technical means. In contrast to the standard approach, the resource-pooling system shall create a reproducible operation with the desired, technically based, repetitious accuracy based on technical means, process flow and process control/operation.

According to the present invention, these objects are achieved particularly through the features of the independent claims. In addition, further advantageous embodiments follow from the dependent claims and the related description.

According to the present invention, the above-mentioned objects for risk sharing of critical illness risks of a variable number of risk exposure components are achieved, particularly, by providing a dynamic self-sufficient risk protection for the risk exposure components by means of the resource-pooling system, wherein the risk exposure components are connected to the resource-pooling system by means of a plurality of payment-receiving modules configured to receive and store payments from the risk exposure components for the pooling of their risks and resources, and wherein the resource-pooling system comprises an event-driven core engine comprising critical illness triggers triggering in a patient dataflow pathway to provide risk protection for a specific risk exposure component based on received and stored payments (of the risk exposure components, in that the total risk of the pooled risk exposure components comprises a first risk contribution of each pooled risk exposure components associated to risk exposure in relation to a first diagnosis of a critical illness, wherein the critical illness is comprised in a predefined searchable table of critical illnesses and wherein critical illness losses occur as a consequence to the first diagnosis of risk exposure components with one of the searchable critical illnesses, in that the total risk of the pooled risk exposure components comprises at least a second and/or successional risk contributions associated to risk exposure in relation to a second and/or successional critical illnesses, wherein the critical illnesses are comprised in the predefined searchable table of critical illness parameters, and wherein a critical illness loss losses occurs as a consequence to the second and/or successional diagnosis of risk exposure components with one of the searchable critical illnesses, and in that in case of a triggering of an occurrence of a first or second or successional critical illness in the patient data flow pathway of a risk exposure component, a loss associated with the first or second or successional critical illness(es) is distinctly covered by the resource pooling system by means of a parametric transfer of payments from the resource-pooling system to the risk exposure component. The critical illness triggers can for example comprise a trigger for triggering the occurrence of measuring parameters indicating heart attack and/or cancer and/or stroke and/or coronary artery by-pass surgery in the patient data flow pathway. Further, the critical illness triggers can e.g. comprise a trigger for triggering the occurrence of measuring parameters indicating Alzheimer's disease, blindness, deafness, kidney failure, major organ transplant, multiple sclerosis, HIV/AIDS contracted by blood transfusion or during an operation, Parkinson's disease, paralysis of limb, terminal illness on the patient dataflow pathway. As an embodiment variant, it can be provided that the first parametric payment, for example can technically be implemented in that it only is transferred by the triggering of the occurrence of measuring parameters indicating the critical illness of malignant cancer and/or a smaller incidence for ductal carcinoma in situ (DCIS) and/or early prostate carcinoma. Further, acute treatment phase parameters indicating surgery and/or chemotherapy and/or radiotherapy and/or reconstructive surgery can be triggered on the patient data flow pathway by means of a critical illness trigger by the core engine. As an embodiment variant, it is provided that a second parametric payment is transferred due to the triggering of acute treatment phase parameters indicating surgery and/or chemotherapy and/or radiotherapy and/or reconstructive surgery. Additionally, recovery phase parameters associated with terminal prognosis data can e.g. be triggered in a patient data flow pathway by means of a critical illness trigger of the core engine. As a further embodiment variant, a third parametric payment is transferred by the triggering of the recovery phase parameters and/or terminal prognosis parameters. As a further variant, the critical illness data of the patient dataflow pathway of the risk exposure component can e.g. additionally be transferred to an automated employee assistance system (EAP: Employee Assistance Program) providing automated support to the risk exposure component. Alternatively or in addition, the critical illness data of the patient dataflow pathway of the risk exposure component can e.g. be transferred to an alert system of a Change Advisory Board (CAB) to activate automated or at least semi-automated, CAB actions. It can also be advantageously that the patient dataflow pathway is e.g. monitored by the resource-pooling system by capturing patient-measuring parameters of the patient data flow pathway at least periodically and/or within predefined time frames or periods. Finally, the patient data flow pathway can e.g. be dynamically monitored by the resource-pooling system in that it triggers patient-measuring parameters of the patient dataflow pathway transmitted from associated measuring systems. The invention has, inter alia, the advantage that the system provides the technical means to meet customer needs related to the financial hardships at the time of the diagnosis of a critical illness, which will become more acute as the treatment progresses. Therefore, cancer fears and the related consequences that are suffered by many people can be met with the automated resource-pooling system according to the invention. The system has, furthermore, the advantage that smaller payments than in traditional critical illness systems are sufficient to allow for a safe operation of the system. The operational aspects of the system are transparent for operators as well as covered risk units, since payment is transferred in response to certain triggers on the cancer patient's information pathways. The system is able to provide an adaptable survival period e.g. 14, 21 or 28 days, to be confirmed or defined by the risk transfer. The system is further able to provide the technical implementation of an automated system that is based on a drawdown payment operation or a predefined payment operation. The system also provides the technical means, which can support different underwriting options, such as (i) underwritten with a set of questions, (ii) in/out underwriting, (iii) inclusion or exclusion of Pre-Existing Condition Exclusion (PECE) and/or a Related Conditions Exclusion with the associated problems of risk transfer. PECE-problems are based on the fact that resource-pooling systems are often required by an employer to create safety provisions, if there is a diagnosis of a critical illness in an employee, in order to provide a lump sum benefit for an employee (or the employee's spouse or children, if comprised in the risk transfer), who is diagnosed with one of the defined medical conditions or undergoes one of the listed surgical procedures. However, many systems fail to take over risk transfers if the individual suffered from the insured condition, before the risk transfer was activated (this is known as the Pre-Existing Condition Exclusion), or because the individual suffered from a condition that led to a claim under the insured illness—for example, it was known that an individual suffered from high blood pressure before the risk transfer being activated, and suffered a stroke after the risk transfer had been activated. Another advantage of the system is based on the fact that payments are directly transferred to the risk transfer unit or the consumer/client. Therefore, the system is able to enhance critical illness insurance offerings by independent financial advisers (IFA). IFAs are persons who give impartial advice to clients on financial matters and who are not employed by any financial institution, although commissions for the sale of products may be received. Especially the IFA service is made completely cost-transparent to the consumer.

In an embodiment variant, the above-mentioned objects for risk sharing of critical illness risks of a variable number of risk exposure components are achieved, particularly, by providing a dynamic self-sufficient risk protection for the risk exposure components by means of the critical illness insurance system based on a resource-pooling system, in that risk-related component data are processed by an assembly module of the resource-pooling system and the likelihood of said risk exposure is provided by means of the assembly module for one or a plurality of the pooled risk exposure components based on the risk-related component data, wherein the risk exposure components are connected to the resource-pooling system by means of a plurality of payment receiving modules, and payment data are received and stored by means of a payment data store from the risk exposure components for the pooling of their risks, and wherein the resource-pooling system triggers a patient dataflow pathway by means of critical illness triggers of an event-driven core engine in order to provide risk protection for a specific risk exposure component based on received and stored payments from the risk exposure components, in that a first risk contribution of each pooled risk exposure components related to a first diagnosis of a critical illness is associated with risk exposure of each pooled risk exposure component, and the total risk of the pooled risk exposure components is determined by means of the resource-pooling system, wherein the critical illness is comprised in a predefined searchable table of critical illnesses, and wherein critical illness losses occur as a consequence of the first diagnosis of risk exposure components due to any one of the searchable critical illnesses, in that a first risk contribution of each of the pooled risk exposure components related to a second and/or successional risk contribution diagnosis of a critical illness is associated with risk exposure of each pooled risk exposure component, and the total risk of the pooled risk exposure components is determined by means of the resource-pooling system, wherein the critical illness is comprised in the predefined searchable table of critical illnesses, and wherein critical illness losses occur as a consequence of the second and/or successional diagnosis of risk exposure components due to any one of the searchable critical illnesses, in that, in case an occurrence of a first or second or successional critical illness on the patient data flow pathway of a risk exposure component is triggered, a corresponding trigger-flag is set by means of the resource-pooling system and a parametric draw-down transfer of payments is assigned to this corresponding trigger-flag, wherein a loss associated with the first or second or successional critical illness is distinctly covered by the resource-pooling system based on the respective trigger-flag and based on the received and stored payment parameters from risk exposure components by the parametric draw-down transfer from the resource-pooling system to the risk exposure component, and in that a first parametric payment is transferred by the triggering of the occurrence of the critical illness, a second parametric payment is transferred by the triggering of an acute treatment phase, and a third parametric payment is transferred by the triggering of a recovery phase associated with terminal prognosis data. This embodiment variant has the advantage of further providing a parametric draw-down payment. It is clear to a man skilled in the art, that the present system can easily be expanded to comprise more than the herein described three trigger-levels.

In one embodiment variant, the receiving and preconditioned storage of payments from risk exposure components for the pooling of their risks is dynamically determined based on total risk and/or the likelihood of the risk exposure of the pooled risk exposure components. This embodiment variant has, inter alia, the advantage that the operation of the resource-pooling system can be dynamically adapted to changing conditions of the pooled risk, as, for example, changing demographic conditions or changing age distributions or the like of the pooled risk components. A further advantage is that the system needs no manual adaption, when it is operated in different environments, places or countries, because the size of the payments of the risk exposure components is directly related to the totally pooled risk.

In another embodiment variant, the number of pooled risk exposure components is dynamically adapted, by means of the resource-pooling system, to a range where non-covariant occurring risks covered by the resource-pooling system affect only a relatively small proportion of the total pooled risk exposure components at a given time. This variant has, inter alia, the advantage that the operational and financial stability of the system can be improved.

In a further embodiment variant, the critical illness triggers are dynamically adapted by means of an operating module based on time-correlated incidence data for a critical illness condition and/or diagnosis or treatment conditions indicating improvements in diagnosis or treatment. This variant has, inter alia, the advantage that improvements in diagnosis or treatment can be dynamically captured by the system and dynamically affect the overall operation of the system based on the total risk of the pooled risk exposure components.

In yet another embodiment variant, the first, second and third parametric payment are leveled by a predefined total payment sum determined at least based on the risk-related component data and/or on the likelihood of the risk exposure for one or a plurality of the pooled risk exposure components based on the risk-related component data, and wherein the first parametric payment that is transferred is up to 30% of said total payment sum, and the second parametric payment that is transferred is up to 50% of said total payment sum, and the third parametric payment that is transferred is up to the left over part given by said total payment sum, minus the actual first parametric payment and the second parametric payment. The predefined total payments can e.g. be leveled to any appropriate lump sum, such as, for example, $50,000 up to $500,000, or any other sum related to the total transferred risk and the amount of the periodic payments of the risk exposure component. As embodiment variant of the realization of the system, the critical illness trigger e.g. can comprise multi-dimensional trigger channels, wherein each of said trigger-flags is assigned to a first dimension trigger channel, comprising a first trigger-level triggering occurrence parameters of the critical illness, a second trigger-level triggering acute treatment phase parameters, and a third trigger-level triggering recovery phase parameters associated with terminal prognosis data, and each of said trigger-flags is assigned to at least a second or higher dimension trigger channel, and comprises additional trigger-stages based on the first, second and/or third trigger-level of the first dimension trigger channel. As a further variant, the critical illness trigger can also comprise multi-dimensional trigger channels, wherein each of said trigger-flags is assigned to a first dimension of a trigger channels comprising a first trigger-level relative to triggering occurrence parameters of the critical illness, a second trigger-level relative to triggering acute treatment phase parameters, and a third trigger-level relative to triggering recovery phase parameters associated with terminal prognosis data, and each of said trigger-flags is assigned to a second dimension of trigger channels comprising a first trigger-level triggering on a first stage of progression-measuring parameters of the occurred critical illness, and one or more higher trigger-levels triggering on higher stages of progression-measuring parameters of the occurred critical illness. This variant, inter alia, has the advantage that the draw-down payments or the payments of predefined amounts, which depend on the first, second or third trigger level, i.e. the different stages of triggers, allow for an adapted payment of the total sum that is dependent on the stage of the critical illness, as triggered by the system.

In one embodiment variant, a periodic payment transfer from the risk exposure components to the resource pooling system via a plurality of payment receiving modules is requested by means of a monitoring module of the resource-pooling system, wherein the risk transfer or protection for the risk exposure components is interrupted by the monitoring module when the periodic transfer is no longer detectable by means of the monitoring module. As a variant, the request for periodic payment transfer can be interrupted automatically or waived by means of the monitoring module, when the occurrence of indicators for critical illness is triggered in the patient data flow pathway of a risk exposure component. These embodiment variants have, inter alia, the advantage that the system allows for a further automation of the monitoring operation, especially of its operation with regard to the pooled resources.

In a further embodiment variant, an independent verification critical illness trigger of the resource pooling system is activated in cases of a triggering of the occurrence of indicators for critical illness in the patient data flow pathway of a risk exposure component by means of the critical illness trigger and wherein the independent verification critical illness trigger additionally is triggering for the occurrence of indicators regarding critical illness in an alternative patient data flow pathway with independent measuring parameters from the primary patient data flow pathway in order to verify the occurrence of the critical illness at the risk exposure component. As a variant, the parametric draw-down transfer of payments is only assigned to the corresponding trigger-flag, if the occurrence of the critical illness at the risk exposure component is verified by the independent verification critical illness trigger. These embodiment variants have, inter alia, the advantage that the operational and financial stability of the system can thus be improved. In addition, the system is rendered less vulnerably relative to fraud and counterfeit.

In addition to the system, as described above, and the corresponding method, the present invention also relates to a computer program product that includes computer program code means for controlling one or more processors of the control system in such a manner that the control system performs the proposed method; and it relates, in particular, to a computer program product that includes a computer-readable medium containing therein the computer program code means for the processors.

BRIEF DESCRIPTION OF THE DRAWINGS

The present invention will be explained in more detail, by way of example, with reference to the drawings in which.

DETAILED DESCRIPTION OF THE PREFERRED EMBODIMENTS

Figure 1:
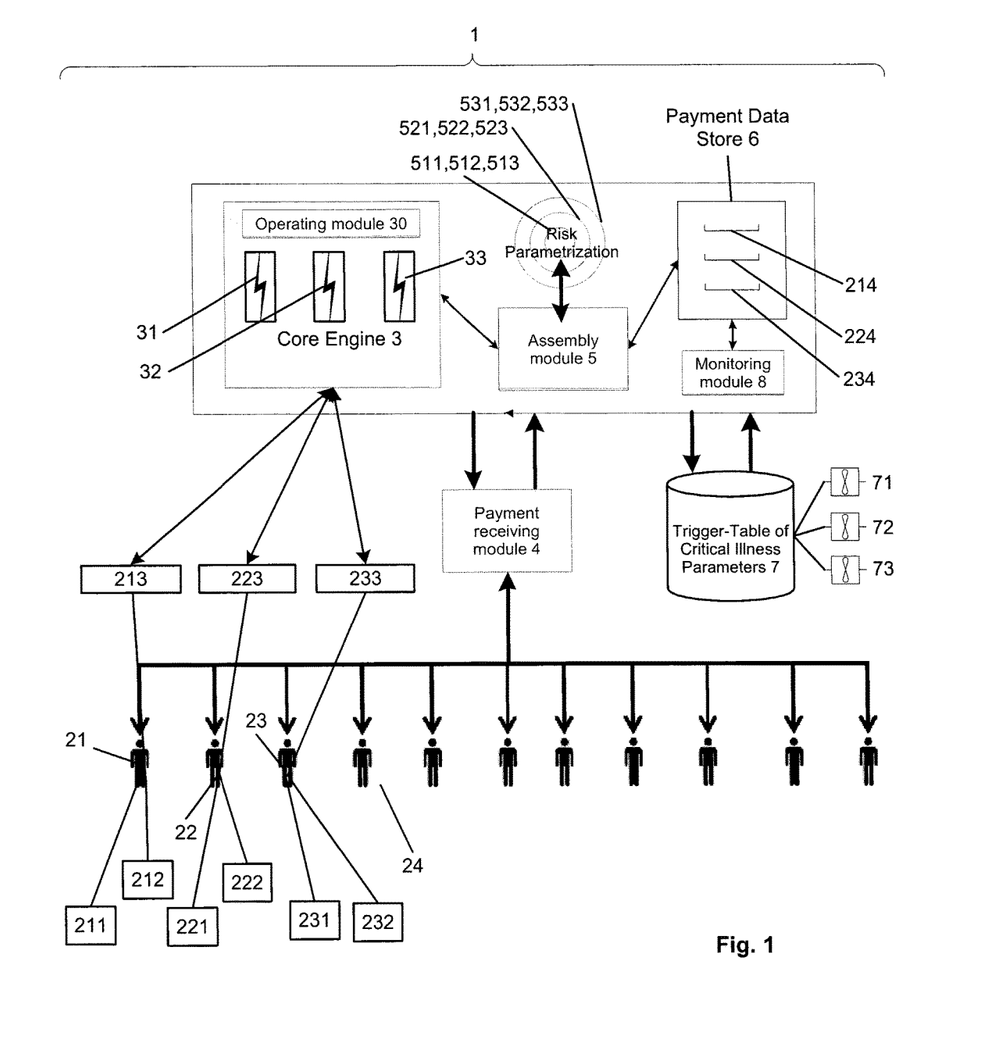
FIG. 1 shows a block diagram illustrating schematically an exemplary parametric, event-driven critical illness insurance system based on a resource-pooling system 1 according to the invention for risk sharing of critical illness risks of a variable number of risk exposure components 21, 22, 23 by providing a dynamic self-sufficient risk protection for the risk exposure components 21, 22, 23. The resource-pooling system 1 comprises an assembly module 5 to process risk-related component data 211, 221, 231 and to provide the likelihood 212, 222, 232 of said risk exposure for one or a plurality of the pooled risk exposure components 21, 22, 23, wherein the risk exposure components 21, 22, 23 are connected to the resource-pooling system 1 by means of a plurality of payment receiving modules 4 that are configured to receive and store 6 payments 214, 224, 234 from the risk exposure components 21, 22, 23 for the pooling of their risks, and wherein the resource-pooling system 1 comprises an event-driven core engine 3 that comprises critical illness triggers 31, 32, 33, which trigger a patient data flow pathway 213, 223, 233 to provide risk protection for a specific risk exposure component 21, 22, 23. The patient data flow pathway 213, 223, 233 is monitored by the resource-pooling system 1 in that patient measuring parameters of the patient data flow pathway 213, 223, 233 are captured, wherein the patient data flow pathway 213, 223, 233 is dynamically monitored and triggered for patient measuring parameters of the patient data flow pathway 213, 223, 233, which is transmitted from associated measuring systems.

FIG. 1 illustrates, schematically, an architecture for a possible implementation of an embodiment of the parametric, event-driven resource-pooling system 1 for risk sharing of critical illness risks. In FIG. 1, reference numeral 1 refers to the resource-pooling system for risk sharing of the risk exposure components 21, 22, 23 .... The resource-pooling system 1 provides a dynamic self-sufficient risk protection and corresponding risk protection structure for a variable number of risk exposure components 21, 22, 23, i.e.; persons or individuals, by its means. The system 1 includes at least one processor and associated memory modules. The system 1 can also include one or more display units and operating elements, such as a keyboard, and/or graphical pointing devices as a computer mouse. The resource-pooling system 1 is a technical device comprising electronic means that can be used by service providers in the field of risk transfer or insurance technology for risk transfer related to critical illness risks (CI). The invention seeks to technically capture, handle and automate complex related operations of the insurance industry. An other aspect is to synchronize and adjust such operations based on technical means. In contrast to the standard approach, the resource-pooling system also achieves an reproducible operations with the desired technical, repetitious accuracy because it is completely based on technical means, process flow and process control/operation.

The resource-pooling system 1 comprises an assembly module 5 to process risk related component data 211, 221, 231 and to provide the likelihood 212, 222, 232 of said risk exposure for one or a plurality of the pooled risk exposure components 21, 22, 23, etc. based on the risk-related component data 211, 221, 231. The resource-pooling system 1 can be implemented as a technical platform, which is developed and implemented to provide critical illness risk transfer through a plurality of (but at least one) payment receiving module 4. The risk exposure components 21, 22, 23, etc. are connected to the resource-pooling system 1 by means of the plurality of payment receiving modules 4 configured to receive and store payments 214, 224, 234 from the risk exposure components 21, 22, 23, ... for the pooling of their risks in a payment data store 6. The storage of the payments can be implemented by transferring and storing component-specific payment parameters. The payment amount can be dynamically determined by means of the resource-pooling system 1 based on total risk of the overall pooled risk exposure components 21, 22, 23. For the pooling of the resources, the resource-pooling system 1 can comprise a monitoring module 8 requesting a periodic payment transfer from the risk exposure components 21, 22, 23, etc. to the resource-pooling system 1 by means of the plurality of payment receiving modules 2, wherein the risk protection for the risk exposure components 21, 22, 23, ... is interrupted by the monitoring module 8, when the periodic transfer is no longer detectable by means of the monitoring module 8. In one embodiment variant, the request for periodic payment transfers is automatically interrupted or waived by means of the monitoring module 8, if the occurrence 1001 of indicators for critical illness 71, 72, 73 is triggered 31 in the patient data flow pathway of a risk exposure component 21, 22, 23, . . . .

As also illustrated schematically in FIG. 1, the resource-pooling system 1 includes a data storing module for capturing the risk-related component data and multiple functional modules; e.g., namely the payment receiving modules 4, the core engine 3 with the triggers 31, 32, 33, the assembly module 5 or the operating module 30. The functional modules can be implemented at least partly as programmed software modules stored on a computer readable medium, connected as fixed or removable to the processor(s) of system 1 or to associated automated systems. One skilled in the art understands, however, that the functional modules can also be implemented fully by means of hardware components, units and/or appropriately implemented modules. As illustrated in FIG. 1, system 1 can be connected via a network, such as a telecommunications network, to the payment receiving module 4. The network can include a wired or wireless network; e.g., the Internet, a GSM network (Global System for Mobile Communication), an UMTS network (Universal Mobile Telecommunications System) and/or a WLAN (Wireless Local Region Network), and/or dedicated point-to-point communication lines. In any case, the technical electronic money schemes for the present system comprises adequate technical, organizational and procedural safeguard means in order to prevent, contain and detect threats to the security of the scheme, particularly the threat of counterfeits. The resource-pooling system 1 comprises further all necessary technical means for electronic money transfer and association e.g. initiated by one or more associated payment receiving modules 4 over an electronic network. The monetary parameters can be based on all possible electronic and transferable means as e.g. e-currency, e-money, electronic cash, electronic currency, digital money, digital cash, digital currency, or cyber currency etc., which can only be exchanged electronically. The payment data store 6 provides the means for associating and storing monetary parameters associated with a single of the pooled risk exposure components 21, 22, 23. The present invention can involve the use of the mentioned network, such as e.g. computer networks or telecommunication networks, and/or the Internet and digital stored value systems. Electronic funds transfer (EFT), direct deposit, digital gold currency and virtual currency are further examples of electronic money. Also, the transfer can involve technologies, such as financial cryptography and technologies enabling the same. For the transaction of the monetary parameters, it is preferable that hard electronic currency is used without the technical possibilities for disputing or reversing any charges. The resource-pooling system 1 supports, for example, non-reversible transactions. The advantage of this arrangement is that the operating costs of the electronic currency system are greatly reduced by not having to resolve payment disputes. However, this way, it is also possible for electronic currency transactions to clear instantly, making the funds available immediately to the system 1. This means that using hard electronic currency is more akin to a cash transaction. However, also conceivable is the use of soft electronic currency, such as currency that allows for the reversal of payments, for example having a "clearing time" of 72 hours, or the like. The way of the electronic monetary parameter exchange applies to all connected systems and modules related to the resource-pooling system 1 of the present invention, such as e.g. the payment receiving module 4. The monetary parameter transfer to the resource-pooling system 1 can be initiated by a payment-receiving module 4 or on request of the resource-pooling system 1.

The resource-pooling system 1 comprises an event-driven core engine 3 comprising critical illness triggers 31, 32, 33 for triggering component-specific measuring parameters in the patient data flow pathway 213, 223, 233 of the assigned risk exposure components 21, 22, 23, . . . . The patient data flow pathway 213, 223, 233 can e.g. be monitored by the resource-pooling system 1, capturing patient-related measuring parameters of the patient data flow pathway 213, 223, 233 at least periodically and/or within predefined time periods. The patient data flow pathway 213, 223, 233 can, for example, also be dynamically monitored by the resource-pooling system 1, by triggering patient-measuring parameters of the patient data flow pathway 213, 223, 233 transmitted from associated measuring systems. Triggering the patient data flow pathway 213, 223, 233, which comprises dynamically recorded measuring parameters of the concerned risk exposure components 21, 22, 23, . . . , the system 1 is able to detect the occurrence of a critical illness and dynamically monitor the different stages during the progress of the critical illness in order to provide appropriately adapted and gradated risk protection for a specific risk exposure component 21, 22, 23, . . . . Such a risk protection structure is based on received and stored payments 214, 224, 234 from the related risk exposure component 21, 22, 23, . . . and/or related to the total risk of the resource-pooling system 1 based on the overall transferred critical illness risks of all pooled risk exposure components 21, 22, 23, . . . .

Figure 2:
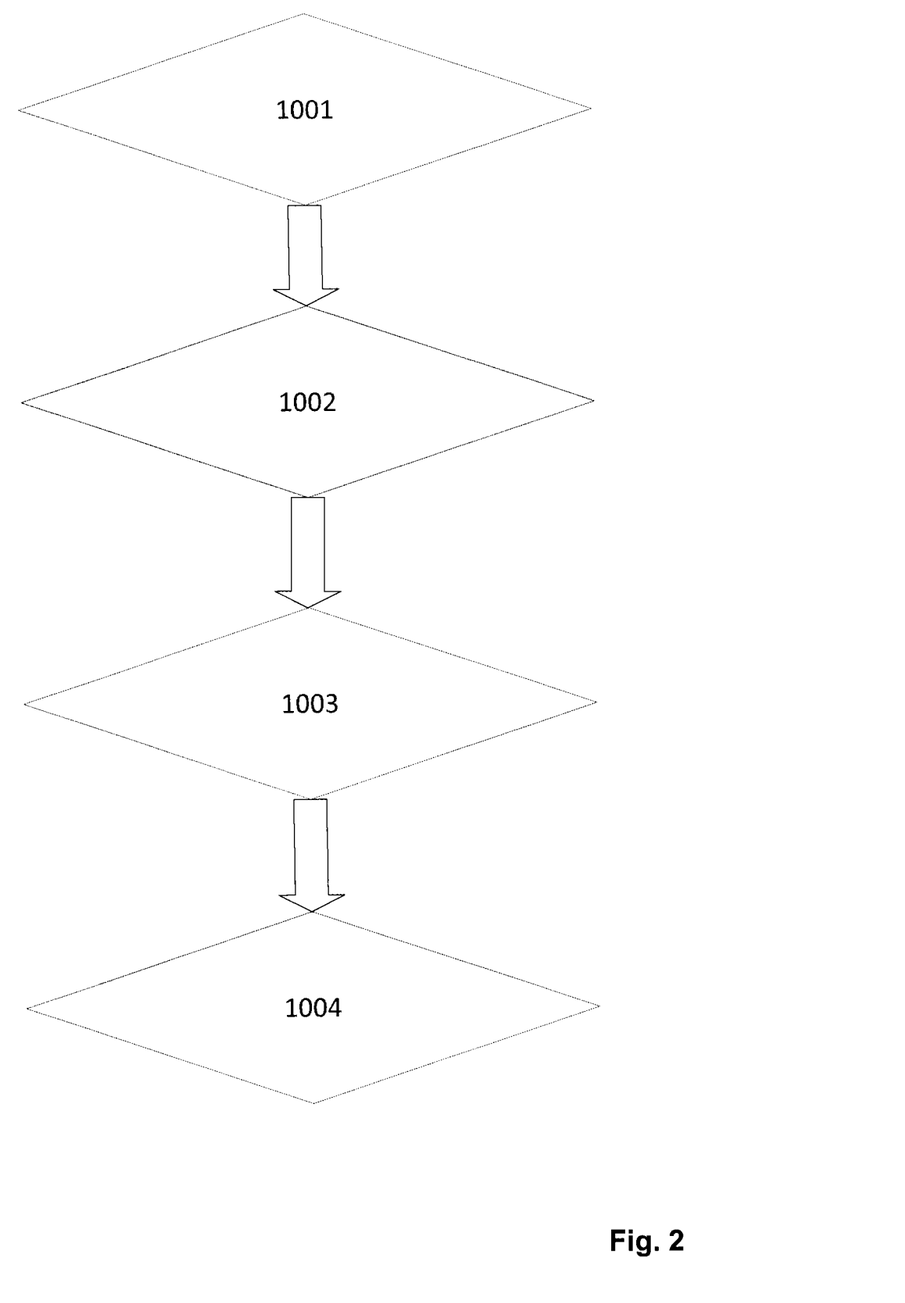
FIG. 2 shows a block diagram illustrating schematically exemplary trigger stages of the resource-pooling system, wherein reference number 1001 is assigned to the triggering of the critical illness, for example the malignant cancer. Reference number 1002 designates the triggering of the treatment phase, such as, for example, surgery, chemotherapy, radiotherapy or medications of drugs etc. Reference number 1003 designates the triggering of the recovery phase or the triggering of the terminal illness and/or the aftercare phase. Finally, reference number 1004 designates the triggering of additional support services. Reference number 1004 gives an example of additional trigger stages to the critical illness triggers 31, 32, 33 of the core engine module 3.

FIG. 2 shows a block diagram with possible trigger stages, wherein reference number 1001 is assigned to the triggering of the critical illness, for example cancer; reference number 1002 designates the triggering of the treatment phase, such as, for example, surgery, chemotherapy, radiotherapy or the administration of medication, etc.; reference number 1003 designates the triggering of the recovery phase or the triggering of the terminal illness and/or the aftercare phase; and reference number 1004 designates the triggering of additional support services. Reference number 1004 gives an example of additional trigger stages to the critical illness triggers 31, 32, 33 of the core engine module 3. The critical illness triggers 31, 32, 33 can e.g. comprise a trigger 31 for triggering the occurrence 1001 of the measuring parameters, indicating a heart attack and/or cancer and/or a stroke and/or coronary artery by-pass surgery in the patient data flow pathway 213, 223, 233. Further, the critical illness triggers 31, 32, 33 can comprise a trigger 31 for triggering the occurrence 1001 of measuring parameters indicating Alzheimer's disease, blindness, deafness, kidney failure, major organ transplant, multiple sclerosis, HIV/AIDS contracted by blood transfusion or during an operation, Parkinson's disease, paralysis of limb, terminal illness in the patient data flow pathway 213, 223, 233. The majority of cases of occurrences of critical illness are typically related to heart attack, stroke and cancer, as can be expected. The average age of individual 21, 22, 23, at which a critical illness can be detected in the patient data flow pathway 213, 223, 233, is ±41 years; however, this depends on the development of diagnostic and other medical means. These statistics are common for all countries where statistics are maintained. However, it is of great concern to observe the increasing number of critical illness occurrences—particularly regarding cancer cases. In most countries, this observed increase is more than 50%, and in some even 80%. Earlier diagnosis due to better diagnostic equipment may be partially responsible for this. Therefore, to ensure proper operation of the resource-pooling system 1, the definitions of the stored trigger parameters 71, 72, 73 of critical illness in the trigger table 7 can be dynamically adapted based on a monitoring of changing risks in the risk exposure components 21, 22, 23. In particular, the trigger parameters 71, 72, 73 can be region-specific, country-specific and/or specific of the total pooled risk, adapted or changed. New critical illnesses 71, 72, 73 can be added, while others can be deleted from the triggerable list of critical illnesses by the resource-pooling system, owing to better treatments or other changed environmental conditions. In one embodied variant, the critical illness triggers 31, 32, 33 can be dynamically adapted by means of an operating module 30, based on time-correlated incidence dates of a critical illness condition and/or diagnosis or treatment conditions indicating improvements in diagnosis or treatment.

In addition to the adaptation of the triggers 31, 32, 33, the amount of requested payments from the risk exposure components 21, 22, 23 can be accordingly adjusted by the resource-pooling system 1. Therefore the receiving and preconditioned storage 6 of payments 214, 224, 234 from risk exposure components 21, 22, 23, . . . for the pooling of their risks can be determined dynamically, based on total risk 50 and/or the likelihood of the risk exposure of the pooled risk exposure components 21, 22, 23, . . . . To improve operational and functional security of the resource-pooling system 1 even further, the number of pooled risk exposure components 21, 22, 23, . . . can be dynamically adapted by means of the resource-pooling system 1 to a range where non-covariant, occurring risks covered by the resource-pooling system 1 affect only a relatively small proportion of the totally pooled risk exposure components 21, 22, 23, . . . at a given time.

The total risk 50 of the pooled risk exposure components 21, 22, 23, . . . comprises a first risk contribution 511, 521, 531 of each pooled risk exposure component 21, 22, 23, . . . that is associated with risk exposure in relation to a first diagnosis of a critical illness. The triggering parameters 71, 72, 73 of the covered critical illnesses is comprised and stored in a predefined searchable table 7, such as e.g. an appropriately structured hash table, of critical illnesses 71, 72, 73, respectively critical illness parameters 71, 72, 73. The critical illness losses occur as a consequence to the first diagnosis of risk exposure components 21, 22, 23, . . . with regard to one of the searchable critical illnesses; i.e., the possible need of a risk exposure components 21, 22, 23, . . . to be covered by the pooled resources of the resource-pooling system 1 is linked to the risk of the occurrence of a critical illness requiring complex medical treatment and handling.

The total risk 50 of the pooled risk exposure components 21, 22, 23, . . . comprises at least a second risk contribution 512,522,523 and/or third or additional successional risk contributions 513/521/ . . . 51$i$/52$i$/53$i$; i.e., up to the i-th risk contribution, associated with risk exposure in relation to a second and/or successional critical illness(es). The critical illnesses 71, 72, 73 for triggering the second risk contribution 512, 522, 523 and/or third or additional successional risk contributions 513/521/ . . . 51$i$/52$i$/53$i$ are the same as for the first risk contribution and comprised in the predefined searchable table 7 of critical illness parameters 71, 72, 73.

Figure 4:
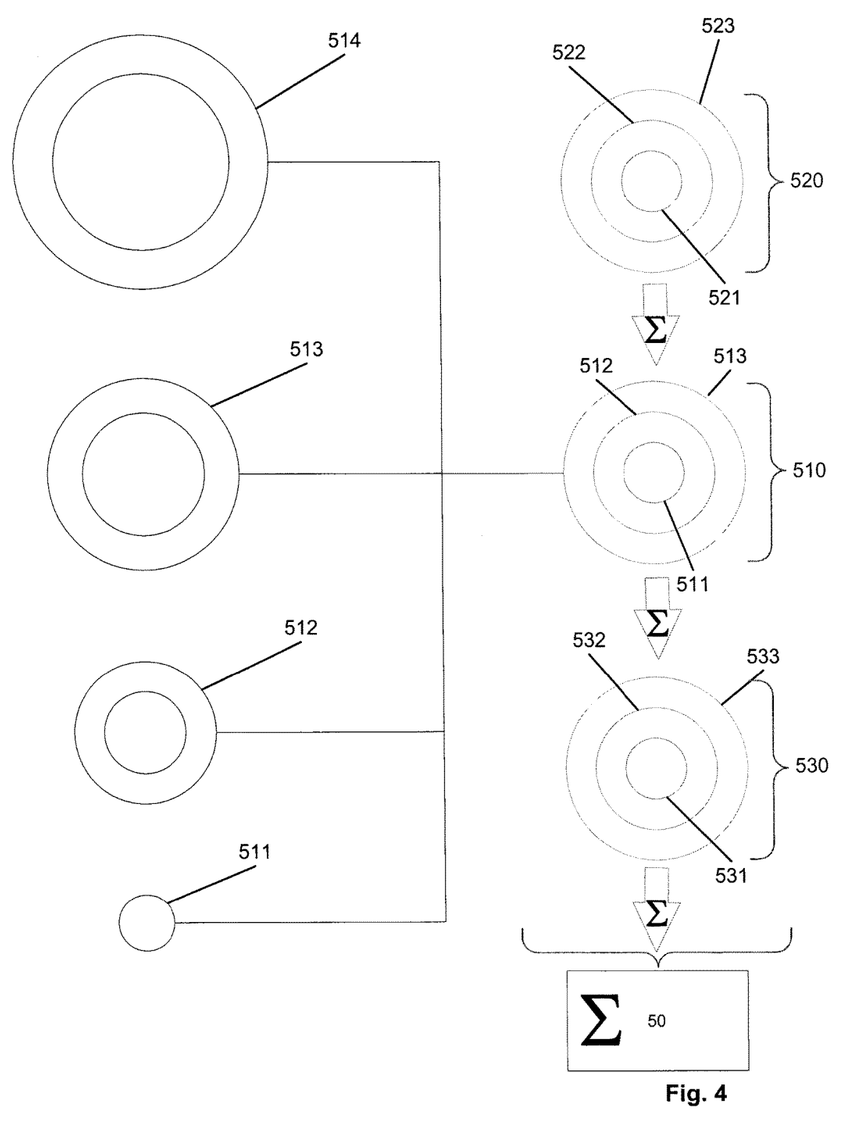
FIG. 4 shows a block diagram illustrating schematically an exemplary parameterization of the risk exposure for critical illness of the risk exposure components 21, 22, 23. The reference numeral 520 gives the total transferred risk of a specific risk exposure component 21, 22, 23 comprising at least a first risk contribution 511, 521, 531 for a first occurrence of a critical illness. Further, it comprises a second risk contribution 512, 522, 532 related to a second occurrence of a critical illness. It also can comprise third 513, 523, 533 and subsequent 51$i$, 52$i$, 53$i$ risk contributions thereafter; i.e., "i" herein denotes the i-th risk distribution.

FIG. 4 shows a block diagram with an exemplary parameterization of the risk exposure for critical illness of the risk exposure components 21, 22, 23. The reference numeral 520 gives the total transferred risk of a specific risk exposure component 21, 22, 23 comprising at least a first risk contribution 511, 521, 531 for a first occurrence of a critical illness. Further comprised is a second risk contribution 512, 522, 532 related to a second occurrence of a critical illness. Also comprised can be a third 513, 523, 533 and subsequent 51$i$,52$i$,53$i$ risk contribution; i.e., "i" denotes the i-th risk distribution.

In case of triggering an occurrence of a first or second or successional critical illness 71,72,73 on the patient dataflow pathway 213,223,233 of a risk exposure component 21, 22, 23, i.e. if a triggering of an occurrence of a first or second or successional critical illness 71, 72, 73 goes into effect in the patient data flow pathway 213, 223, 233, a corresponding trigger-flag is set by means of the resource-pooling system 1 and a parametric draw-down or predefined transfer of payments is assigned to this corresponding trigger-flag. A loss associated with the first or second or successional critical illness(es) 71, 72, 73 is distinctly covered by the resource-pooling system 1, based on the respective trigger-flag and based on the received and stored payment parameters 214, 224, 234 from risk exposure components 21, 22, 23 by the parametric draw-down or predefined transfer from the resource-pooling system 1 to the risk exposure component 21, 22, 23, etc. The payment receiving module 4 can, as an input device, comprise one or more data processing units, displays and other operating elements, such as a keyboard and/or a computer mouse or another pointing device. As mentioned previously, the receiving operation of the payments with regard to the risk exposure components 21, 22, 23 is monitored based on the stored component-specific payment parameters in the payment data store 6. The different components of the resource-pooling system 1, such as e.g. the payment receiving module 4 with the core engine 3 and the assembly module 5 can be connected via a network for signal transmission. The network can comprise, e.g., a telecommunications network, such as a wired or wireless network, e.g., the Internet, a GSM network (Global System for Mobile Communications), an UMTS network (Universal Mobile Telecommunications System) and/or a WLAN (Wireless Local Area Network), a Public Switched Telephone Network (PSTN) and/or dedicated point-to-point communication lines. The payment receiving module 4 and/or core engine 3 and the assembly module 5 can also comprise a plurality of interfaces for connecting to the telecommunications network adhering to the transmission standard or protocol. As an embodied variant, the payment receiving module 4 can also be implemented as an external device relative to the resource-pooling system 1, which provides the risk transfer service via the network for signal transmission, e.g. by a secured data transmission line.

A first parametric payment 211 is transferred by triggering the occurrence 1001 of the critical illness 71, 72, 73 by means of the critical illness trigger 31 of the core engine 3, thus triggering the measuring parameters of the specific risk exposure component 21, 22, 23 in the related patient data flow pathway 213, 223, 233. The core engine 3, analogously to the resource-pooling system 1 and the other components of the system, is implemented based on underlying electronic components, steering codes and interacting interface devices, such as e.g. appropriate signal generation modules or other modules interacting electronically by means of appropriate signal generation between the different modules, devices, or the like. For example, the first parametric payment can be transferred by triggering 31 the occurrence 1001 of measuring parameters indicating the critical illness 71, 72, 73 of malignant cancer and/or smaller incidence of ductal carcinoma in situ (DCIS) and/or early prostate carcinoma.

A second parametric payment 212 is transferred by triggering measuring parameters in the patient data flow pathway 213, 223, 233 indicating the initiation of an acute treatment phase 1002 by means of the critical illness trigger 32 of the core engine 3. For example, acute treatment phase parameters 1002 indicating surgery and/or chemotherapy and/or radiotherapy and/or reconstructive surgery can be triggered in patient data flow pathway 213, 223, 233 by means of a critical illness trigger 32 of the core engine 3. For example, the second parametric payment can only be transferred by triggering 32 acute treatment phase parameters 1002, indicating surgery and/or chemotherapy and/or radiotherapy and/or reconstructive surgery. Finally a third parametric payment 213 is transferred by triggering measuring parameters in the patient data flow pathway 213, 223, 233 indicating the initiation of a recovery phase 1003 linked to terminal prognosis data by means of the critical illness trigger 33 by the core engine 3. For example, recovery phase parameters 1003 linked to or associated with terminal prognosis data are triggered in patient data flow pathway 213, 223, 233 by means of a critical illness trigger 33 by the core engine 3. As a variant, the third parametric payment is only transferrable by triggering 33 recovery phase parameters and/or terminal prognosis parameters 1003.

Figure 3:
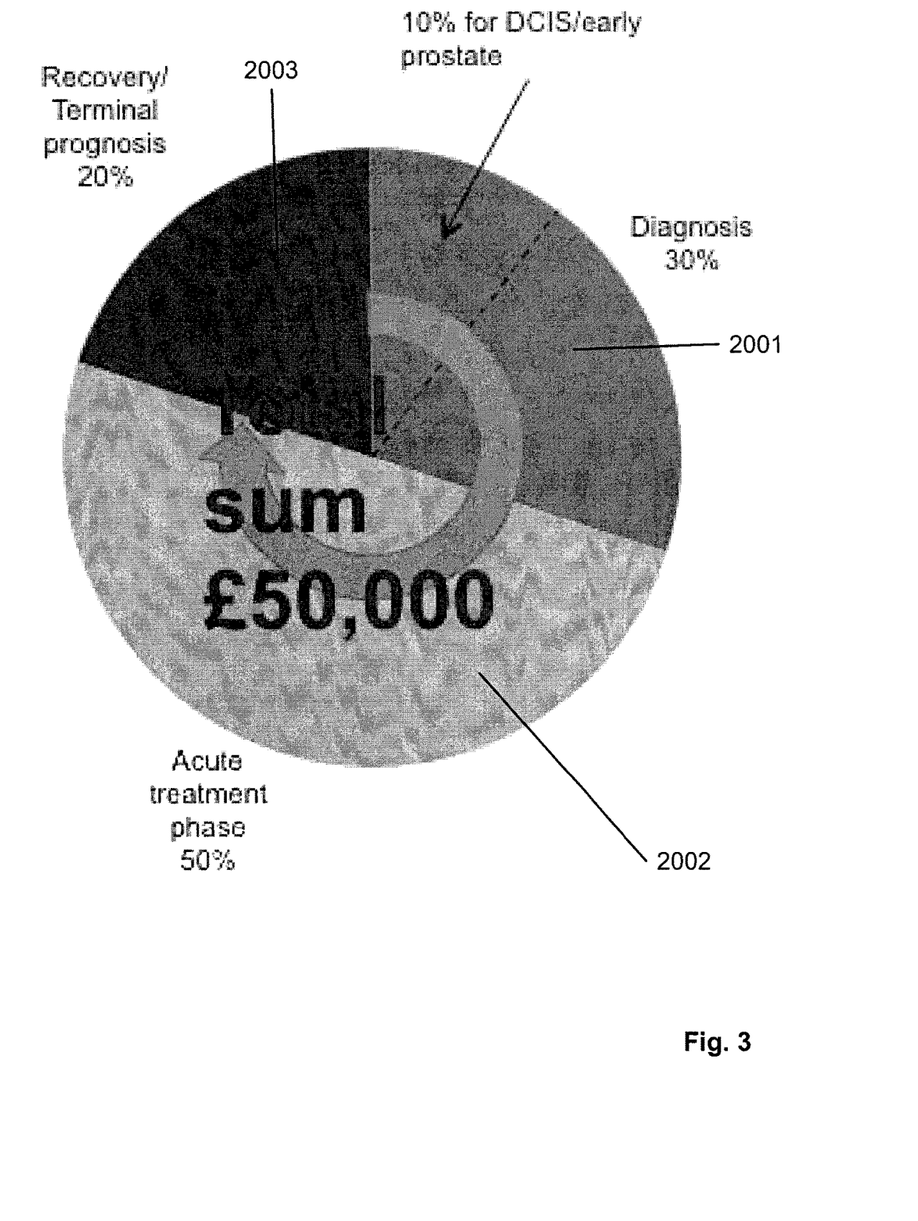
FIG. 3 shows a diagram illustrating schematically an exemplary payment drawdown as it can be provided by the resource pooling system 1 in case of triggering critical illness at a risk exposure component.

Therefore, if triggering 1001 takes effect, an occurrence of a first critical illness 71, 72, 73 in the patient dataflow pathway 213, 223, 233 of a risk exposure component 21, 22, 23, any associated loss is covered by the resource-pooling system 1 based on the received and stored payments 214, 224, 234 from risk exposure components 21, 22, 23 by transferring a parametric diagnosis payment 2001 from the resource-pooling system 1 to the risk exposure component 21, 22, 23, etc.; if triggering 1002 takes effect, an occurrence of an acute treatment phase in the patient data flow pathway 213, 223, 233 of an associated loss is covered by the resource-pooling system 1 based on the received and stored payments 214, 224, 234 from risk exposure components 21, 22, 23 by transferring a parametric treatment phase payment 2002 from the resource-pooling system 1 to the risk exposure component 21, 22, 23, etc.; and if triggering 1003 takes effect, an occurrence of a recovery phase linked to terminal prognosis data in the patient data flow pathway and associated loss is covered by the resource-pooling system based on the received and stored payments 214, 224, 234 from risk exposure components 21, 22, 23 by transferring a parametric recovery phase payment 2003 from the resource-pooling system 1 to the risk exposure component 21, 22, 23, etc. The first, second and third parametric payments can, for example, be leveled by a predefined total payment sum determined at least based on the risk-related component data 211, 221, 231 and/or the likelihood of the risk exposure for one or a plurality of the pooled risk exposure components 21, 22, 23, etc., based on the risk-related component data 211, 221, 231, wherein the first parametric payment is transferred up to 30% of said total payment sum, and the second parametric payment is transferred up to 50% of said total payment sum, and the third parametric payment is transferred up to the residual part given by said total payment sum minus the actual first parametric payment and the second parametric payment. Such an exemplary payment draw-down as it can be provided by the resource-pooling system 1 in the event of a triggering of a critical illness at a risk exposure component is shown in the diagram of FIG. 3.

As a further technical variant, the critical illness triggers 31, 32, 33 comprise multi-dimensional trigger channels. Each of said trigger-flags is assigned to a first dimension trigger channel comprising a first trigger-level triggering 31 on occurrence parameter 1001 of the critical illness 71, 72, 73, a second trigger-level triggering 32 on acute treatment phase parameter 1002, and a third trigger-level triggering 33 on recovery phase parameter 1003 linked to or associated with terminal prognosis data; and each of said trigger-flags is assigned to at least a second or higher dimension trigger channel and comprises additional trigger-stages based on the first, second and/or third trigger-levels of the first dimension trigger channel. The critical illness trigger 31, 32, 33 can e.g. comprise multi-dimensional trigger channels, wherein each of said trigger-flags is assigned to a first dimension of a trigger channel comprising a first trigger-level triggering 31 on occurrence parameter 1001 of the critical illness 71, 72, 73, a second trigger-level triggering 32 on acute treatment phase parameter 1002, and a third trigger-level triggering 33 on recovery phase parameter 1003 linked to terminal prognosis data, and each of said trigger-flags is assigned to a second dimension of a trigger channel comprising a first trigger-level triggering 31 on a first stage of progression-measuring parameters of the occurrence 1001 with regard to critical illness 71, 72, 73, and one or more higher trigger-levels triggering 32, 33 in higher stages of progression-measuring parameters of the occurred critical illness 71, 72, 73.

In addition, the resource-pooling system 1 can be realized such that it transfers critical illness data in the patient data flow pathway 213, 223, 233 of the related risk exposure component 21, 22, 23, etc., after triggering the occurrence of a critical illness 71, 72, 73, to an automated employee assistance system (EAP: Employee Assistance Program) providing automated support to the risk exposure component 21, 22, 23, etc. Analogously, by triggering the occurrence of a critical illness 71, 72, 73 by means of the critical illness trigger 31 by the core engine 3, critical illness data in the patient data flow pathway 213, 223, 233 of the related risk exposure component 21, 22, 23, etc. can be transferred to an alert system of an Change Advisory Board (CAB) to activate automated or at least semi-automated CAB actions.

Finally, in a further specified embodied variant, an independent verification critical illness trigger of the resource-pooling system 1 can be activated in the event of a triggering of the occurrence 1001 of indicators for critical illness 71, 72, 73 in the patient data flow pathway 213, 223, 233 of a risk exposure component 21, 22, 23, etc. by means of the critical illness trigger 31, and wherein the independent verification critical illness trigger additionally is triggering with regard to the occurrence 1001 indicators for critical illness 71, 72, 73 in an alternative patient data flow pathway 215, 225, 235 with independent measuring parameters from the primary patient data flow pathway 213, 223, 233 to verify the occurrence 1001 of the critical illness 71, 72, 73 at the risk exposure component 21, 22, 23, etc, As a variant, the parametric draw-down or predefined transfer of payments is only assigned to the corresponding trigger-flag, if the occurrence 1001 of the critical illness 71, 72, 73 at the risk exposure component 21, 22, 23, etc. is verified by the independent verification critical illness trigger.

REFERENCES

1 Resource-pooling system/Critical illness insurance system
21, 22, 23 Risk exposure component
211, 221, 231 Risk-related component data
212, 222, 232 Likelihood of risk exposure of the pooled risk exposure components
213, 223, 233 Patient dataflow pathway
214, 224, 234 Stored payment parameters
215, 225, 235 Alternative patient dataflow pathway
3 Core engine
30 Operating module
31, 32, 33 Critical illness triggers
4 Payment receiving modules
5 Assembly module
50 Total Risk
511, 521, 531 First risk contribution
512, 522, 532 Second risk contribution
513, 523, 533 Third risk contribution
51$i$, 52$i$, 53$i$ i-th risk contribution
6 Payment data store
7 Trigger table with critical illness parameter
71, 72, 73 Critical illness parameters
8 Monitoring module
1001 Diagnosis phase of the critical illness
1002 Treatment phase (surgery, chemotherapy/radiotherapy/medication)
1003 Recovery phase and/or terminal illness phase and/or aftercare phase
1004 Additional support services
2001, 2002, 2003 Parametric payment transfers from the system 1 to the risk exposure units 21, 22, 23

The invention claimed is:

1. A completely automated, self-adaptable, event-driven critical illness insurance system, based on an automated resource-pooling system for risk sharing of critical illness risks of a plurality of risk exposure components through circuitry of the plurality of risk exposure components by providing a dynamic self-sufficient risk protection for the risk exposure components, comprising:

circuitry configured to implement an automated resource-pooling system comprising:

interfaces to the plurality of risk exposure components, wherein the interfaces comprise a plurality of payment-receiving modules configured to receive and store payments from the risk exposure components for pooling of their risks and resources based on component-specific payment parameters by electronic money transfer by the payment-receiving modules over an electronic network, an event-driven core engine implementing critical illness triggers that trigger a patient dataflow pathway including critical illness data to provide risk protection for a specific risk exposure component based on received and stored payments from the risk exposure components, the patient data flow pathway being dynamically monitored by capturing patient measuring parameters of the patient data flow pathway, and dynamically triggered for patient measuring parameters of the patient data flow pathway, which are transmitted from associated measuring systems, storage storing a predefined searchable table of critical illnesses, an assembly module that processes a total risk of pooled risk exposure components among the plurality of risk exposure components, the total risk comprising a sum of risk contributions, each of the risk contributions being associated with a diagnosis of a critical illness and one of the risk exposure components, the risk contributions comprising a first risk contribution of each pooled risk exposure component associated to risk exposure in relation to a first diagnosis of the critical illness, wherein the critical illness is included in the predefined searchable table of critical illnesses, and wherein critical illness losses occur as a consequence to a first diagnosis of risk exposure components with one of the searchable critical illnesses, wherein the assembly module processes the total risk of pooled risk exposure components to comprise at least a second and/or third or additional successional risk contribution associated to risk exposure in relation to at least a second and/or successional diagnosis of a critical illness, wherein the critical illness is included in the predefined searchable table of critical illnesses, and wherein critical illness losses occur as a consequence to at least a second and/or successional diagnosis of risk exposure components with one of the searchable critical illnesses, the assembly module determines the total risk of the pooled risk exposure, and provides the likelihood of said risk exposure for one or a plurality of the pooled risk exposure components based on the risk-related component data, in a case of a triggering of at least one occurrence of a first or second or successive critical illness in the patient data flow pathway of the specific risk exposure component, the core engine sets a corresponding trigger-flag and assigns a parametric transfer of payments to the corresponding trigger-flag, and a loss associated with the first or second or successive critical illness is distinctly covered by the resource pooling system based on the respective trigger-flag and based on the received and stored payment parameters from the payment-receiving modules via the parametric transfer of payments from the resource-pooling system to the specific risk exposure component, and an operating module that provides the dynamic, self-sufficient risk protection by dynamically adapting an implementation of the critical illness triggers by the event-driven core engine based on time-correlated incidence data for critical illness conditions and/or diagnosis or treatment conditions indicating improvements in diagnosis or treatment capturing at least changing time-correlated environmental or country-specific conditions including changing demographic conditions and/or changing age distributions directly affecting the totally pooled risk, wherein the operating module dynamically determines and adapts receiving and preconditioned storage of payments from the risk exposure components for the pooling of their risks based on total risk and/or the likelihood that the risk exposure of the pooled risk exposure components will occur, and wherein the operating module dynamically adapts the number of pooled risk exposure components by the resource-pooling system to a range where non-covariant occurring risks covered by the resource-pooling system affect fewer than all of the totally pooled risk exposure components at a given time, and wherein the critical illness triggers are dynamically adapted by the operating module based on time-correlated incidence data for a critical illness conditions and/or diagnosis or treatment conditions indicating improvements in diagnosis or treatment.

2. The system according to claim 1, wherein the critical illness triggers comprise a trigger for triggering an occurrence of measuring parameters indicating a heart attack, a cancer, a stroke, or a coronary artery by-pass surgery, or a combination thereof, in the patient dataflow pathway.

3. The system according to claim 1, wherein the critical illness triggers further comprise another trigger for triggering the occurrence of measuring parameters indicating Alzheimer's disease, blindness, deafness, kidney failure, major organ transplant, multiple sclerosis, HIV/AIDS contracted by blood transfusion, HIV/AIDS contracted by blood transfusion during an operation, Parkinson's disease, paralysis of limb, or terminal illness, or a combination thereof, in the patient dataflow pathway.

4. The system according to claim 1, wherein upon each triggering of an occurrence of measuring parameters indicating a critical illness, a total parametric payment is allocated with the triggering, and wherein a first portion of the allocated total parametric payment is transferrable upon said triggering.

5. The system according to claim 1, wherein the critical illness triggers further comprise another trigger for triggering acute treatment phase parameters indicating surgery, chemotherapy, radiotherapy, reconstructive surgery, or a combination thereof, in the patient dataflow pathway.

6. The system according to claim 4, wherein a second portion of the allocated total parametric payment is transferrable upon triggering of acute treatment phase parameters indicating surgery, chemotherapy, radiotherapy, reconstructive surgery, or a combination thereof.

7. The system according to claim 1, wherein the critical illness triggers further comprise another trigger for triggering recovery phase parameters associated with or linked to terminal prognosis data in the patient dataflow pathway.

8. The system according to claim 6, wherein a third portion of the allocated total parametric payment is transferrable upon triggering of a recovery phase parameter and/or a terminal prognosis parameter.

9. The system according to claim 8, wherein the first portion of the allocated total parametric payment, the second portion of the allocated total parametric payment, and the third portion of the allocated total parametric payment sum up to the allocated total parametric payment.

10. The system according to claim 9, wherein the allocated total parametric payment is determined at least based on the risk-related components data and/or on the likelihood of the risk exposure for at least one of the pooled risk exposure components based on the risk related components data, and
wherein the first portion of the allocated total parametric payment is transferred up to 30% of said total payment sum, the second portion of the allocated total parametric payment is transferred up to 50% of said total payment sum, and the third portion of the allocated total parametric payment is transferred up to a residual percentage of said total payment sum given by said total payment sum minus an actual portion of the allocated total parametric payment and the second portion of the allocated total parametric payment.

11. The system according to claim 1,
wherein the automated resource-pooling system further comprises a monitoring module for requesting a periodic payment transfer from the risk exposure components via the plurality of payment receiving modules, and
wherein the monitoring module interrupts the risk protection for the risk exposure components when the periodic payment transfer is no longer detectable by the monitoring module.

12. The system according to claim 11, wherein the request for periodic payment transfer is interrupted or waived by the monitoring module when an occurrence of indicators for critical illness is triggered in the patient data flow pathway of the specific risk exposure component.

13. The system according to claim 1, wherein the circuitry is further configured to activate an independent verification critical illness trigger, in the event of an occurrence of indicators for critical illness in the patient dataflow pathway of the specific risk exposure component, via a critical illness trigger, and which additionally is a triggering for an occurrence of indicators for critical illness in an alternative patient dataflow pathway with independent measuring parameters from the patient data flow pathway, to verify the occurrence of indicators for critical illness at the specific risk exposure component.

14. The system according to claim 13, wherein the parametric transfer of payments is only assigned to the corresponding trigger-flag, if the occurrence of indicators for critical illness at the specific risk exposure component is verified by the independent verification critical illness trigger.

15. The system according to claim 1, wherein critical illness data of the patient dataflow pathway of the specific risk exposure component are transferred to an automated employee assistance system ("EAP") configured to provide automated support to the specific risk exposure component.

16. The system according to claim 1, wherein the circuitry is further configured to monitor the patient dataflow pathway by capturing a patient measuring parameter of the patient dataflow pathway at least periodically and/or within predefined time frames.

17. The system according to claim 1, wherein the circuitry is further configured to dynamically monitor the patient dataflow pathway by a triggering of patient measuring parameters of the patient dataflow pathway transmitted from associated measuring systems.

18. A completely automated, self-adaptable method for risk sharing of critical illness risks of a plurality of risk exposure components through circuitry of the plurality of risk exposure components by providing a dynamic self-sufficient risk protection for the risk exposure components via an automated resource-pooling system comprising circuitry, the method comprising:
connecting the risk exposure components to the resource pooling system via interfaces comprising a plurality of payment-receiving modules configured to receive and store payments from the risk exposure components for pooling of their risks and resources based on component-specific payment parameters by electronic money transfer by the payment receiving modules over an electronic network;
storing a predefined searchable table of critical illnesses;
triggering, using the circuitry, via an event-driven core engine comprising critical illness triggers, a patient dataflow pathway including critical illness data to provide risk protection for a specific risk exposure component based on received and stored payments from the risk exposure components, the patient data flow pathway being dynamically monitored by capturing patient measuring parameters of the patient data flow pathway, and dynamically triggered for patient measuring parameters of the patient data flow pathway, which are transmitted from associated measuring systems,
wherein a total risk of pooled risk exposure components among the plurality of risk exposure components comprises a sum of risk contributions, each of the risk contributions being associated with a diagnosis of a critical illness and one of the risk exposure components, the risk contributions comprising a first risk contribution of each pooled risk exposure component associated to risk exposure in relation to a first diagnosis of the critical illness, wherein the critical illness is included in the predefined searchable table of critical illnesses, and wherein critical illness losses occur as a consequence to a first diagnosis of risk exposure components with one of the searchable critical illnesses,
wherein the total risk of pooled risk exposure components comprises at least a second and/or third or additional successional risk contribution associated to risk exposure in relation to at least a second and/or successional diagnosis of a critical illness, wherein the critical illness is included in the predefined searchable table of critical illnesses, and wherein critical illness losses occur as a consequence to at least a second and/or successional diagnosis of risk exposure components with one of the searchable critical illnesses, and
wherein the total risk of the pooled risk exposure is determined, and the likelihood of said risk exposure for one or a plurality of the pooled risk exposure is provided components based on the risk-related component data,
wherein, in a case of a triggering of at least one occurrence of a first or second or successive critical illness in the patient data flow pathway of the specific risk exposure component, a corresponding trigger-flag is set, a parametric transfer of payments is assigned to the corresponding trigger-flag, and a loss associated with the first or second or successive critical illness is distinctly covered by the resource pooling system based on the respective trigger-flag and based on the received and stored payment parameters from the payment-receiving modules via the parametric transfer of payments from the resource-pooling system to the specific risk exposure component, and providing the dynamic, self-sufficient risk protection, wherein an implementation of the critical illness triggers by the event-driven core engine is dynamically adapted by an operating module based on time-correlated incidence data for critical illness conditions and/or diagnosis or treatment conditions indicating improvements in diagnosis or treatment capturing at least changing time-correlated environmental or country-specific conditions including changing demographic conditions and/or changing age distributions directly affecting the totally pooled risk, wherein the receiving and preconditioned storage of payments from risk exposure components for the pooling of their risks is dynamically determinable and adapted based on total risk and/or the likelihood that the risk exposure of the pooled risk exposure components will occur, and wherein the number of pooled risk exposure components is dynamically adaptable by the resource-pooling system to a range where non-covariant occurring risks covered by the resource-pooling system affect fewer than all of the totally pooled risk exposure components at a given time, and wherein the critical illness triggers are dynamically adapted by the operating module based on time-correlated incidence data for a critical illness conditions and/or diagnosis or treatment conditions indicating improvements in diagnosis or treatment.

19. The method according to claim 18, wherein the triggering further comprising triggering, using the circuitry, an occurrence of measuring parameters indicating a heart attack, a cancer, a stroke, or a coronary artery by-pass surgery, or a combination thereof, in the patient dataflow pathway.

20. The method according to claim 19, wherein the triggering further comprising triggering, using the circuitry, the occurrence of measuring parameters indicating Alzheimer's disease, blindness, deafness, kidney failure, major organ transplant, multiple sclerosis, HIV/AIDS contracted by blood transfusion, HIV/AIDS contracted by blood transfusion during an operation, Parkinson's disease, paralysis of limb, or terminal illness, or a combination thereof, in the patient dataflow pathway.

21. The method according to claim 18, wherein upon each triggering of an occurrence of measuring parameters indicating a critical illness, a total parametric payment is allocated with the triggering, and wherein a first portion of the allocated total parametric payment is transferrable upon said triggering.

22. The method according to claim 18, wherein the critical illness triggers further comprise another trigger for triggering acute treatment phase parameters indicating surgery, chemotherapy, radiotherapy, reconstructive surgery, or a combination thereof, in the patient dataflow pathway.

23. The method according to claim 21, a second portion of the allocated total parametric payment is transferrable upon triggering of acute treatment phase parameters indicating surgery, chemotherapy, radiotherapy, reconstructive surgery, or a combination thereof.

24. The method according to claim 18, wherein the critical illness triggers further comprise another trigger for triggering recovery phase parameters associated with or linked to terminal prognosis data in the patient dataflow pathway.

25. The method according to claim 23, wherein a third portion of the allocated total parametric payment is transferrable upon triggering of a recovery phase parameter and/or a terminal prognosis parameter.

26. The method according to claim 25, wherein the first portion of the allocated total parametric payment, the second portion of the allocated total parametric payment, and the third portion of the allocated total parametric payment sum up to the allocated total parametric payment.

27. The method according to claim 26, wherein the allocated total parametric payment is determined at least based on the risk-related components data and/or on the likelihood of the risk exposure for at least one of the pooled risk exposure components based on the risk related components data, and wherein the first portion of the allocated total parametric payment is transferred up to 30% of said total payment sum, the second portion of the allocated total parametric payment is transferred up to 50% of said total payment sum, and the third portion of the allocated total parametric payment is transferred up to a residual percentage of said total payment sum given by said total payment sum minus an actual portion of the allocated total parametric payment and the second portion of the allocated total parametric payment.

28. The method according to claim 18, further comprising:

requesting, using the circuitry via a monitoring module, a periodic payment transfer from the risk exposure components via a plurality of payment receiving modules, wherein the risk protection for the risk exposure components is interrupted by the monitoring module when the periodic payment transfer is no longer detected by the monitoring module.

29. The method according to claim 28, wherein the request for periodic payment transfer is interrupted or waived by the monitoring module when an occurrence of indicators for critical illness is triggered in the patient data flow pathway of the specific risk exposure component.

30. The method according to claim 18, further comprising:

activating, using the circuitry, an independent verification critical illness trigger, in the event of an occurrence of indicators for critical illness in the patient dataflow pathway of the specific risk exposure component, via a critical illness trigger, and which additionally is a triggering for an occurrence of indicators for critical illness in an alternative patient dataflow pathway with independent measuring parameters from the patient data flow pathway, to verify the occurrence of indicators for critical illness at the specific risk exposure component.

31. The method according to claim 30, wherein the parametric transfer of payments is only assigned to the corresponding trigger-flag, if the occurrence of indicators for critical illness at the specific risk exposure component is verified by the independent verification critical illness trigger.

32. The method according to claim 18, wherein critical illness data of the patient dataflow pathway of the specific risk exposure component are transferred to an automated employee assistance system ("EAP") configured to provide automated support to the specific risk exposure component.

33. The method according to claim 18, further comprising monitoring, using the circuitry, the patient dataflow pathway by capturing a patient measuring parameter of the patient dataflow pathway at least periodically and/or within pre-defined time frames.

34. The method according to claim 18, further comprising dynamically monitoring, using the circuitry, the patient dataflow pathway by a triggering of patient measuring parameters of the patient dataflow pathway transmitted from associated measuring systems.

* * * * *